United States Patent [19]  
Klosa

[11] 4,393,236  
[45] Jul. 12, 1983

[54] PRODUCTION OF NONHYGROSCOPIC SALTS OF 4-HYDROXYBUTYRIC ACID

[76] Inventor: Joseph Klosa, Jänickestrasse 13, D-1000 Berlin 37, Fed. Rep. of Germany

[21] Appl. No.: 282,419

[22] Filed: Jul. 13, 1981

[30] Foreign Application Priority Data

Jul. 17, 1980 [DE] Fed. Rep. of Germany ....... 3027390  
Nov. 20, 1980 [DE] Fed. Rep. of Germany ....... 3049869

[51] Int. Cl.$^3$ ............................................. C07C 59/00  
[52] U.S. Cl. .................................... 562/579; 424/317  
[58] Field of Search ........................ 562/579; 424/317

[56] References Cited

FOREIGN PATENT DOCUMENTS 465270 5/1950 Canada ................................ 562/579  
39-6962 11/1964 Japan ................................... 562/579  
922029 3/1963 United Kingdom ................ 562/579

*Primary Examiner*—Paul J. Killos  
*Attorney, Agent, or Firm*—Horst M. Kasper

[57] ABSTRACT

A method for the production of nonhygroscopic magnesium and/or calcium salts of 4-hydroxybutyric acid. A member of the group consisting of magnesium hydroxide, magnesium oxide, magnesium carbonate, calcium hydroxide, calcium oxide and calcium carbonate is reacted with 4-hydroxybutyric acid and/or 4-butyrolactone in an aqueous solution. The solution is crystallized at a sufficiently low temperature for producing a solid nonhygroscopic salt. Waterfree calcium-4-hydroxybutyrate and waterfree as well as hydrated magnesium-4-hydroxybutyrate are added to pharmaceutically acceptable carrier or filler material for production of tranquilizing and/or sleeping drugs.

21 Claims, No Drawings

PRODUCTION OF NONHYGROSCOPIC SALTS OF 4-HYDROXYBUTYRIC ACID

BACKGROUND OF THE INVENTION

1. Field of the Invention

The present invention relates to the production of nonhygroscopic alkaline earth salts of 4-hydroxybutyric acid suitable in the production of pharmaceutical preparations.

2. Brief Description of the Background of the Invention Including Prior Art

It is known that 4-hydroxy-butyric acid is liquid and a crystalline form can ony be obtained with difficulty. Also 4-hydroxybutyric acid is not available commercially in a pure composition. The sodium salts of the 4-hydroxybutyric acid are hygroscopic. The calcium salts known from British Pat. No. 922,029 of the 4-hydroxybutyric acid have been disclosed as being suitable for application only in liquid form in solution. A melting point for the calcium salt was not provided, presumably because it could not be determined based on the strong hygroscopicity. According to British Pat. No. 922,029 the hygroscopic calcium salt is obtained by reacting 4-butyrolactone with a solution of calciumhydroxide. This is a general method of operation, however the reaction is very violent and strongly exothermic, such that side reactions can occur resulting in final products which are difficult or not all suitable for crystallization. Presently completely unknown are magnesium salts of γ-hydroxybutyric acid.

Therefor, up to now a general and wider therapeutic application was excluded for the 4-hydroxybutyric acid and its salts be it in the form of tablets, dragees and/or capsules. Based on the difficulties of production and handling of the 4-hydroxy-butyric acid and its salts, these are also very expensive.

It is further known that 4-hydroxybutyric acid has narcotic effects. It is successfully applied in medicine as an intravenously injectable anesthetic in the form of the sodium salt. The sodium salt, depending on the dose, generates a sleeping state from which the patient can be waked up.

However the free 4-hydroxybutyric acid as well as its sodium salt and the calcium salt taught in British Pat. No. 922,029 have not been applicable on a broad scale in pharmacy because of their strong hygroscopic action.

However, there is a large desire for these materials especially as sleeping agent and as a tranquilizer, since virtually all the known sleeping agents and tranquilizers such as barbiturates, amides, but also diazepams are associated with large side effects upon continuous application, but also directly associated with undesired aftereffects. In particular all present sleeping agents and tranquilizers interfere in an undesirable way with the metabolism of the nerves and this is also true for the plant derived agents such as those of valerian. Especially they are transformed into uncontrollable metabolites with obscure action and they frequently damage the liver irreversibly.

It is in fact known from the non-poisonous 4-hydroxybutyric acid that it acts as a sleeping drug (compare G. Kuschinsky, Taschenbuch der modernen Arzneibehandlung, 8th edition, 1980, page 328), however a handy oral application in the form of tablets, dragees or capsules of the compounds known in this respect has been impossible up to now because of the strong hygroscopicity of the known compounds. Even as solutions the known compounds were not exactly measurable as a dose, since hygroscopic materials always rapidly attract water, even upon weighing, such that in large scale production of pharmaceutical agents constant doses cannot be maintained.

SUMMARY OF THE INVENTION

1. Purposes of the Invention

It is an object of the present invention to provide non-hygroscopic salts of 4-hydroxy-butyric acid.

It is another object of the present invention to provide a salt of 4-hydroxybutyric acid suitable for producing solid and/or liquid pharmaceutical compositions.

It is another object of the present invention to provide salts of 4-hydroxybutyric acid, which do not act burning and etching to the mucous membrane of the mouth.

These and other objects and advantages of the present invention will become evident from the description which follows.

2. Brief Description of the Invention

The present invention provides a waterfree calcium-4-hydroxybutyrate $Ca(COOCH_2CH_2CH_2OH)_2$. The present invention further provides magnesium-4-hydroxybutyrate $Mg(COOCH_2CH_2CH_2OH)_2$, which can be free of water of hydration, which can comprise 4 molecules of water of hydration for each molecule of $Mg(COOCH_2CH_2CH_2OH)_2$ and/or which can comprise about 5 molecules of water of hydration for each molecule of $Mg(COOCH_2CH_2CH_2OH)_2$.

There is also provided a method for the production of magnesium and/or calcium salts of 4-hydroxybutyric acid which comprises reacting a member of the group consisting of 4-hydroxybutyric acid, 4-butyrolactone and mixtures thereof with a member of the group consisting of magnesium hydroxide, magnesium oxide, magnesium carbonate, calcium hydroxide, calcium oxide, calcium carbonate and mixtures thereof in an aqueous solution, and crystallizing the resulting solution at a temperature sufficiently low to produce a solid nonhygroscopic salt. Before and/or during the crystallizing step a nonsolvent for the respective calcium or magnesium 4-hydroxybutyrate can be added to the aqueous solution and a preferred nonsolvent is acetone. Preferably waterfree calcium-4-hydroxy butyrate is crystallized at a temperature of less than about 80° C. Calcium-4-hydroxybutyrate can be recrystallized from an organic solution to provide nonhygroscopic, nonhydrated calcium-4-hydroxybutyrate.

Magnesium-4-hydroxybutyrate can be crystallized at a temperature below about 40° C. to obtain a nonhygroscopic salt containing about 5 moles of water for each molecule of magnesium-4-hydroxybutyrate. The magnesium-4-hydroxybutyrate hydrated with about 5 molecules of water for each molecule $Mg(COOCH_2CH_2C-H_2OH)_2$ can be dried to provide $Mg(COOCH_2CH_2C-H_2OH)_2 \cdot 4H_2O$ containing about 4 molecules of water of hydration for each molecule of magnesium-4-hydroxybutyrate.

The hydrated calcium and/or magnesium salts of 4-hydroxybutyric acid can be dried to a nonhygroscopic product of $(Ca,Mg)(COOCH_2CH_2CH_2OH)_2$ free of water of hydration. The magnesium butyrate can be crystallized from an aqueous solution at a temperature up to about the boiling point of water.

There is also provided a pharmaceutical composition which comprises a nonhygroscopic salt of 4-hydroxybutyric acid and a pharmaceutically acceptable carrier and/or filler material.

The invention accordingly consists in the compositions, methods of preparation and applications which will be exemplified in the method and compositions of matter hereinafter described and of which the scope of application will be indicated in the appended claims.

DESCRIPTION OF INVENTION AND PREFERRED EMBODIMENTS

In accordance with the present invention it was surprisingly found that both the water-free calcium salts of the 4-hydroxybutyric acid as well as the magnesium salts of this acid are not hygroscopic and are suitable for unlimited storage. The present invention provides in one aspect a method for the production of non-hygroscopic salts of the 4-hydroxybutyric acid characterized in that either (a) 4-hydroxybutyric acid is neutralized with hydroxides, oxides or carbonates of magnesium or calcium in an aqueous solution or (b) 4-butyrolactone is hydrolytically split with an hydroxide, oxide or carbonate of calcium or magnesium according to the reaction formula

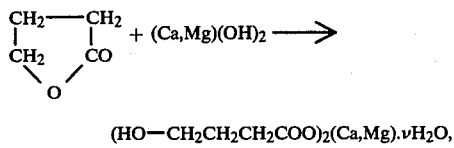

$$(HO-CH_2CH_2CH_2COO)_2(Ca,Mg) \cdot \nu H_2O,$$

where $\nu = 0$, 4, 5 or 6, whereupon the use of calcium hydroxide, calcium oxide or calcium carbonate temperatures below 80° C. and preferably temperatures from about 40° C. to 60° C. are employed, and whereupon the use of magnesiumhydroxide, magnesium oxide or magnesium carbonate temperatures around the boiling point of water are employed.

The waterfree calcium salt of the 4-hyxdroxybutyric acid in accordance with the present invention has a constant melting point of from about 166° to 168° C. and even after hours of storage at air no water is attracted, that is the salt remains completely dry. It was found in accordance with the present invention that it can be obtained in crystalline form already then when 4-butyrolactone is reacted with calcium hydroxide, calcium oxide or calcium carbonate such that the temperature remains below 80° C., and is preferably between 40° and 60° C. The water-free calcium 4-hydroxybutyrate and the waterfree magnesium 4-hydroxybutyrate can be produced by removal of water by drying hydrated calcium 4-hydroxybutyrate and/or magnesium 4-hydroxybutyrate.

As it had been known that water containing calcium salts of the 4-hydroxybutyric acid are hygroscopic, it was the more surprising to find in accordance with the present invention that the magnesium salts of this acid, which were hitherto unknown, are neither in the water-free nor in the hydrated state hygroscopic. The magnesium salts of 4-hydroxybutyric acid according to the present invention can bind up to at most 6 moles of water of crystallization. After short drying in air the water contents is reduced to from about 4 to 5 moles. All these magnesium salts are not hygroscopic, are well suited for being stored and are as well as the above mentioned water-free calcium salt suitable for the preparation of various pharmaceutical preparations.

In particular 4-hydroxybutyric acid derivatives do not show poisonous effects or side effects such as those associated with the known narcotical or tranquilizing compositions. 4-hydroxybutyric acid is completely degraded in the human body and is closely related to the natural metabolites of the body such as lactic acid. In particular, 4-hydroxybutyric acid does not affect the liver as is observed with tranquilizing and hypnotic preparations.

The difficulties encountered with the hygroscopic compunds are eliminated with the non-hygroscopic salts of the 4-hydroxybutyric acid. The materials according to the invention allow without effort to produce solid or liquid forms to be administered and also the disadvantages of the preparations of solutions of free acid and sodium salt are avoided, which act burning and etching on the mucous membrane of the mouth.

It has been found that the nonhygroscopic calcium and magnesium salts of the 4-hydroxybutyric acid are administered in a dose from about 100 to 2000 mg and preferably from about 300 to 500 mg orally as tablets, dragees or capsules and they develop an excellent effect of generating sleep or of tranquilizing. Pharmacological investigations have shown however an excellent analgetic effect of the compounds of the present invention. In combination with pain-relieving agents such as salicylic amide, acetylsalicylic acid or p-acetylaminophenol the analgetic effect is increased. The compounds of the present invention open up new possibilities of pain-relief, such as a possible pain-relieving alternative with the analgesic asthma syndrome. Painful stress as occurs with chronic pains is decreased and eliminated. Therefor, the combination of the invention salts with analgesic and antirheumatically active pharmaceutical preparations is advantageous. Such a combination can be provided without problem with the salts of the present invention in contrast to the known hygroscopic materials, which interact chemically with the combination partners.

The calcium and magnesium salts of the present invention derived from 4-hydroxybutyric acid are solid, nonhygroscopic and storable and they can be recrystallized. They can be pressed to tablets in combination with tablet additives, they can be coated or as a powder they can be filled into capsules. They dissolve in water to a clear solution and they can be dispensed as injection solutions, but also as drops, or in drinks or as suppositories while maintaining a stable situation.

The invention is further illustrated by way of the following examples which are to be considered as examplary and not in a limiting sense.

EXAMPLE 1

A suspension of 37 g calcium hydroxide in 80 ml water is added in portions and under stirring to 86 g 4-butyrolactone. The mixture warms up. The addition of the aqueous calcium hydroxide suspension is controlled such that no boiling occurs. After terminating the addition the colorless reaction product is allowed to stand for several hours. Usually a colorless solution is obtained, otherwise any precipitate is decanted and the colorless, somewhat sirupy solution is freed from water on a water bath, possibly under reduced pressure. The residue crystallizes to a mass of colorless crystals, which is after dried at temperatures from about 60° to 80° C. Yield: about 105 g. Melting point 164°–166° C. The chemical analysis finds 16.21 weight percent calcium (calculated 16.26 weight percent calcium). The product is Di-(4-hydroxybutyric) calcium. It is recrystallized by dissolving in little methanol followed by adding of acetone to cloudiness.

EXAMPLE 2

74 g analytically pure calcium hydroxide are suspended in 200 ml of tap water. 160 ml 4-butyrolactone are added in portions (each portion about 5 to 10 ml) and under stirring to this suspension at room temperature. After addition of 20 ml the reaction mixture warms to about 50° to 60° C. The addition of 4-butyrolactone is controlled such that the temperature remains between about 50° and 60° C., which takes about 1 hour. During this time the calcium hydroxide has dissolved practically completely. The reaction material is contaminated with a slight rust-yellow precipitate. It is thinned down with 300 ml methanol, is left for four hours to itself and is then filtered through a folded filter. The clear filtrate is cautiously treated with 200 ml acetone in the way that after each portion of acetone causing a precipitate time is allowed for the precipitate to redissolve. A water-clear solution is obtained which is placed for crystallization. After two hours of standing colorless crystals start to deposit. In this state the crystallization is accelerated by continuous addition of acetone (in total 100 ml). The crystallization time is 24 hours. The crystals are sucked off and are washed initially with 50 ml methanol and then additionally with 60 ml acetone. The crystals are dried at temperatures from about 60° to 80° C. in a drying cabinet. Yield: 230 g. Melting point 166°–168° C. (immediately). The product is the waterfree nonhygroscopic calcium salt of the 4-hydroxybutyric acid. It is dissolvable as desired in water, the aqueous solution has a pH-value of 7 to 7.5. The salt can be stored as long as desired and does not change in air. Even upon storage no water is attracted from the air.

EXAMPLE 3

As described in Example 2, 74 g calcium hydroxide are reacted with 160 ml 4-butyrolactone in 200 ml water. The sirupy reaction material is thickened by evaporation on a water bath and is allowed to stand for several days such that it crystallizes to a hygroscopic mass of crystals. They are comminuted and are warmed together with 300 ml methanol under stirring on a water bath. The raw calcium salt of the 4-hydroxybutyric acid is not hygroscopic and melts weakly at 164°–166° C. Yield: 204 g. The salt dissolves readily in water, however cloudy contaminants remain. For purification the raw product is dissolved in 500 ml methanol and 80 ml water and then filtered. The water-clear filtrate is compounded with 100 ml methanol and is then under stirring mixed with 400 ml acetone in portions. No precipitate is allowed to occur. After several hours crystallization starts and continues for 24 to 48 hours. The crystals are sucked off and washed initially with 60 ml methanol and then with 100 ml acetone and are dried at 60° to 80° C. Yield: 220 g in analytical quality. Melting point 166°–168° C. Instead of methanol also ethanol and isopropanol can be employed for recrystallization with the same success. Without employing water containing alcohols as recrystallization medium or as additive of the recrystallization and purification no stable and in particular no nonhygroscopic calcium salts are obtained. The percentage of water in the alcohols should be from about 3 to 10 percent by volume.

The such obtained final product does easily dissolve in water, is not hygroscopic and has a pleasant aromatic odor.

EXAMPLE 4

42 g magnesium carbonate in 100 ml water are added to 86 g 4-butyrolactone under stirring and warming on a water bath to about 50° to 62° C. Carbon dioxide developes. After termination of the addition the solution is heated on the water bath an additional 3 to 5 minutes until complete dissolution. Then the water-clear solution is thickened by evaporation in a dish on a water bath. A colorless sirup is obtained, which solidifies if allowed to stand for 14 days. The mass of crystals in a yield of 120 g still contains water of crystallization (melting point 105°–107° C. under effervescence) and the water can be removed by drying at about 60° to 80° C. Melting point 172°–174° C. The analysis showed 10.47 weight percent magnesium (calculated 10.55 weight percent magnesium). The product is the magnesium salt of the 4-hydroxybutyric acid. Sum formula: $C_8H_{14}O_6Mg$ (Molecular weight 230.39). It dissolves easily in water, methanol and ethanol, it does not dissolve in ether and hydrocarbons, it is not hygroscopic, is storable and has a pleasant aromatic odor.

EXAMPLE 5

60 g magnesium hydroxide (pro analysis) are suspended in 200 ml tap water under stirring. In a stream and under stirring 160 ml 4-butyrolactone are mixed into this suspension. Then the mixture is heated on a water bath for 6 hours under stirring in a 2-liter-flask. The magnesium hydroxide dissolves practically completely. The flask is allowed to stand over night, while contaminants deposit and the solution is decanted without effort from the contaminant deposit. The water clear decantate is initially stirred with 100 ml acetone for 10 minutes. The colorless sirupy liquid, which now turned more viscous, is mixed again with 100 ml acetone as described above, the acetone is again removed by decanting and the fairly viscous, colorless sirup is left to itself at room temperature for about 2 to 4 hours. It solidifies to a colorless crystal mass, which is comminuted in a mortar and dried for several hours in air. Melting point 76° to 78° C.

Yield: 314 g in analytically pure from.

Sum formula: $C_8H_{14}O_6Mg.5H_2O$. This magnesium salt contains about 5 mole of water of hydration. It is not hygroscopic, is stable and can be stored for arbitrary long times. By drying over several hours at 40° to 50° C. it loses part of its water (1 mole) of crystallization and then melts at 118° to 120° C.

Waterfree magnesium 4-hydroxybutyrate can be produced by removal of water by sublimation and/or evaporation of water under decreased partial pressure of water and at elevated temperature or by crystallization from a solution containing an organic solvent.

The waterfree salt melts at 172°–174° C. The chemical analysis shows 10.50 weight percent magnesium (calculated 10.55 weight percent magnesium).

All modifications are nonhygroscopic and stable during storage. 1 g of the magnesium salt dissolves in 2 ml water at room temperature, the pH of the aqueous solution is 7.

EXAMPLE 6

Production of tablets:

| | |
|---|---|
| Di(4-hydroxybutyric) calcium | 500 mg |

-continued

| Tablet additive (in conventional manner) | ad 1000 mg |
|---|---|

EXAMPLE 7

Production of capsules:

| D(4-hydroxybutyric) magnesium | 300 mg |
|---|---|
| Lactose | 120 mg |
| Microcrystalline cellulose sold under trademark Avicel by FMC Corp. | 30 mg |
| Highly dispers, pyrogeneous silica containing more than 99.8 percent SiO2 sold under trademark Aerosil 200 by Degussa Corp, Teterboro, N.J. | 2 mg |
| Magnesium stearate | 3 mg |
| Weight of the capsule | 455 mg |

EXAMPLE 8

Production of suppositories:

| Di(4-hydroxybutyric)-calcium | 500 mg |
|---|---|
| Suppository mass, a clear oily hydrocarbon (monolene) | 1500 mg |
| Weight of the suppository | 2000 mg |

EXAMPLE 9

Production of honey liquid: 10 g magnesium salt according to example 4 are mixed into 80 g bee honey. A yellow honey sirup was obtained having a well tasting consistency.

EXAMPLE 10

Tablets against pain:

| Di(4-hydroxybutyric)calcium | 100 mg |
|---|---|
| Salicylic amide | 300 mg |
| Tablet additives | ad 1000 mg |

EXAMPLE 11

Production of dragees:

| Di(4-hydroxybutyric)calcium | 200 mg |
|---|---|
| Phenylbutazone | 100 mg |
| Dragee additive | ad 600 mg |

EXAMPLE 12

Production of capsules

| Di(4-hydroxybutyric)calcium | 200 mg |
|---|---|
| Acetylsalicylic acid | 250 mg |
| Sorbitol | 50 mg |
| Total: | 500 mg |

I claim:

1. Waterfree calcium-4-hydroxybutyrate of the formula $Ca(COOCH_2CH_2CH_2OH)_2$.

2. Magnesium-4-hydroxybutyrate of the formula $Mg(COOCH_2CH_2CH_2OH)_2$.

3. Magnesium-4-hydroxybutyrate according to claim 2 furthermore free from water of hydration.

4. Magnesium-4-hydroxybutyrate according to claim 2 further comprising 4 molecules of water of hydration for each molecule of $Mg(COOCH_2CH_2CH_2OH)_2$ resulting in a composition of the formula $Mg(COOCH_2CH_2CH_2OH)_2.4H_2O$.

5. Magnesium-4-hydroxybutyrate according to claim 2 further comprising 5 molecules of water of hydration for each molecule of $Mg(COOCH_2CH_2CH_2OH)_2$ resulting in a composition of the formula $Mg(COOCH_2CH_2CH_2OH)_2.5H_2O$.

6. A method for the production of magnesium and/or calcium salts of 4-hydroxybutyric acid comprising
reacting a member of the group consisting of 4-hydroxybutyric acid, 4-butyrolactone and mixtures thereof with a member of the group consisting of magnesium hydroxide, magnesium oxide, magnesium carbonate, calcium hydroxide, calcium oxide, calcium carbonate and mixtures thereof in an aqueous solution; and
crystallizing the resulting solution at initial temperatures of from about 40° to 80° C. sufficiently low to produce a solid nonhygroscopic salt.

7. The method according to claim 6 further comprising adding to the aqueous solution a nonsolvent for the respective 4-hydroxybutyrate before and/or during the crystallizing step.

8. The method according to claim 7 wherein the nonsolvent is acetone.

9. The method according to claim 6 further comprising recrystallizing calcium 4-hydroxybutyrate from an organic solution to provide nonhygroscopic, nonhydrated calcium 4-hydroxybutyrate.

10. The method according to claim 6 wherein the crystallizing of the magnesium 4-hydroxybutyrate is performed at a temperature below about 40° C. to obtain a non-hygroscopic salt containing about 5 moles of water for each mole of magnesium 4-hydroxybutyrate $Mg(COOCH_2CH_2CH_2OH)_2$.

11. The method according to claim 10 further comprising drying the magnesium 4-hydroxybutyrate hydrated with about 5 molecules of water for removal of about 1 molecule of water to provide $Mg(COOCH_2CH_2CH_2OH).4H_2O$ containing about 4 molecules of water of hydration for each molecule of magnesium 4-hydroxybutyrate.

12. The method of claim 6 further comprising drying the product according to claim 6 to remove all water of hydration for obtaining a nonhygroscopic salt.

13. A pharmaceutical composition providing narcotic effects comprising
a nonhygroscopic salt of 4-hydroxybutyric acid; and
a pharmaceutically acceptable carrier and/or filler material.

14. A method for the production of magnesium and/or calcium salts of 4-hydroxybutyric acid comprising reacting a member of the group consisting of 4-hydroxybutyric acid, 4 butyrolactone and mixtures thereof with a member of the group consisting of magnesium hydroxide, magnesium oxide, magnesium carbonate, calcium hydroxide, calcium oxide, calcium carbonate and mixtures thereof in an aqueous solution; and crystallizing the resulting material in the presence of a non-solvent at a temperature sufficiently low to produce a solid nonhygroscopic salt.

15. The method according to claim 14 wherein the nonsolvent is acetone.

16. The method according to claim 14 wherein the calcium 4-hydroxy butyrate is crystallized at a temperature of less than about 80° C.

17. The method according to claim 14 further comprising recrystallizing calcium 4-hydroxybutyrate from an organic solution to provide nonhygroscopic, nonhydrated calcium 4-hydroxybutyrate.

18. The method according to claim 14 wherein the crystallizing of the magnesium 4-hydroxybutyrate is performed at a temperature below about 40° C. to obtain a non-hygroscopic salt containing about 5 moles of water for each mole of magnesium 4-hydroxybutyrate $Mg(COOCH_2CH_2CH_2OH)_2$.

19. The method according to claim 18 further comprising drying the magnesium 4-hydroxybutyrate hydrated with about 5 molecules of water for removal of about 1 molecule of water to provide $Mg(COOCH_2CH_2CH_2OH).4H_2O$ containing about 4 molecules of water of hydration for each molecule of magnesium 4-hydroxybutyrate.

20. The method according to claim 14 further comprising drying the product according to claim 16 to remove all water of hydration for obtaining a nonhygroscopic salt.

21. The method according to claim 14 further comprising crystallizing the magnesium 4 hydroxybutyrate from an aqueous solution at a temperature up to about the boiling point of water.

* * * * *